(12) United States Patent
Righi et al.

(10) Patent No.: US 12,306,476 B2
(45) Date of Patent: May 20, 2025

(54) EYE PROTECTION MASK FOR PRACTICING WINTER SPORTS

(71) Applicant: OUT OF S.R.L., Brescia (IT)

(72) Inventors: Federico Righi, Brescia (IT); Roberto Righi, Brescia (IT)

(73) Assignee: OUT OF S.R.L., Brescia (IT)

( * ) Notice: Subject to any disclaimer, the term of this patent is extended or adjusted under 35 U.S.C. 154(b) by 0 days.

(21) Appl. No.: 18/255,901

(22) PCT Filed: Dec. 6, 2021

(86) PCT No.: PCT/IB2021/061359
§ 371 (c)(1),
(2) Date: Jun. 5, 2023

(87) PCT Pub. No.: WO2022/123423
PCT Pub. Date: Jun. 16, 2022

(65) Prior Publication Data
US 2024/0036356 A1 Feb. 1, 2024

(30) Foreign Application Priority Data
Dec. 7, 2020 (IT) .......................... 102020000030104

(51) Int. Cl.
*G02F 1/137* (2006.01)
*G02C 5/00* (2006.01)
(Continued)

(52) U.S. Cl.
CPC ............. *G02C 7/101* (2013.01); *G02C 5/008* (2013.01); *G02F 1/13725* (2013.01);
(Continued)

(58) Field of Classification Search
CPC ............. G02F 1/1333; G02F 1/133308; G02F 1/133311; G02F 1/1335; G02F 1/133526;
(Continued)

(56) References Cited

U.S. PATENT DOCUMENTS 5,172,256 A 12/1992 Sethofer et al.
9,335,565 B2 5/2016 Miller, IV et al.
(Continued)

FOREIGN PATENT DOCUMENTS

CN 210803893 U * 6/2020
CN 111929923 A 11/2020
(Continued)

OTHER PUBLICATIONS

Patent Translate CN 210803893 (Jun. 19, 2020).*
International Search Report for International Patent Application No. PCT/IB2021/061359, mailed Mar. 14, 2022.

*Primary Examiner* — Thoi V Duong
(74) *Attorney, Agent, or Firm* — Armstrong Teasdale LLP

(57) ABSTRACT

An eye mask for practicing winter sports is provided. The eye mask has a lens assembly having a frame, a structural lens, a Guest-Host-type liquid crystal (LC) film adapted to modify a transparency level thereof and laminated to the structural lens, and a photovoltaic cell for supplying the LC film. The structural lens is applied to the frame. The frame has a higher stiffness than the structural lens.

18 Claims, 5 Drawing Sheets

(51) Int. Cl.
 *G02C 7/10* (2006.01)
 *G02F 1/1333* (2006.01)
 *G02F 1/1335* (2006.01)

(52) U.S. Cl.
 CPC .. *G02F 1/133308* (2013.01); *G02F 1/133311* (2021.01); *G02F 1/133526* (2013.01)

(58) Field of Classification Search
 CPC ..... G02F 1/13725; G02C 7/101; G02C 5/008; A61F 9/023
 See application file for complete search history.

(56) References Cited

U.S. PATENT DOCUMENTS

| | | | |
|---|---|---|---|
| 2008/0055538 A1* | 3/2008 | Kobayashi | G02B 1/18 2/436 |
| 2018/0045981 A1 | 2/2018 | Cornelius et al. | |
| 2019/0227347 A1 | 7/2019 | Jimenez et al. | |
| 2020/0200945 A1* | 6/2020 | Totani | C08K 5/5333 |
| 2022/0179237 A1* | 6/2022 | von Blanckenhagen | B29D 11/00865 |

FOREIGN PATENT DOCUMENTS

| | | |
|---|---|---|
| IT | 202000000526 A1 | 7/2021 |
| WO | 2021144684 A1 | 7/2021 |

* cited by examiner

EYE PROTECTION MASK FOR PRACTICING WINTER SPORTS

CROSS-REFERENCE TO RELATED APPLICATION

This application is a National Stage Application of International Patent Application No. PCT/IB2021/061359, having an International Filing Date of Dec. 6, 2021, which claims priority to Italian Patent Application No. 102020000030104 filed Dec. 7, 2020, the entire contents of each of which are incorporated by reference herein.

FIELD OF THE INVENTION

It is an object of this invention to provide an eye protection mask for practicing winter sports, such as skiing, snowboarding and the like.

BACKGROUND OF THE INVENTION

In the practice of skiing and other winter sports, it is necessary to use a protective mask for the eyes, in particular to protect the eyes of practitioners from excessive light radiation caused by the reflection of light on the snow, accentuated by the high altitude.

Therefore, ski masks are widely used, which are configured in such a way as to protect both from excessive light radiation and from the more or less large snow particles that are easily found in suspension in the air, raised by other skiers or by atmospheric precipitations.

When practicing sports, for example when skiing downhill at high speed, crossing wooded areas and open fields, the light conditions change very suddenly, so the need for the mask to be able to vary the level of light radiation filtering is very significant.

Some known solutions attempt to provide a solution to this problem but fail to do so effectively.

There are, for example, ski masks equipped with photochromic lenses that are able to change their transparency according to the amount of light received; however, these lenses change their physical properties too slowly, so they are almost useless when the light radiation changes very suddenly.

Ski masks equipped with electrochromic lenses are also known; however, these lenses also change their physical properties too slowly and also need to be powered by batteries, as the change of state occurs in the presence of a difference in electrical potential. The need for batteries is understandably a major drawback for use as a sports mask, as it increases the weight and bulk, requires recharging, and presents a degeneration of performance over the life cycle of the product.

The Applicant, meanwhile, is the holder of Italian patent application No. 10 2020 000 000 526, which relates to a mask equipped with Guest Host (GH)-type LCD lenses, powered by solar cells. Such a mask is proving particularly effective.

Despite the excellent performance shown by the aforesaid mask, the Applicant has found, due to accurate practical tests, that the user's vision may not be optimal in certain circumstances.

SUMMARY OF THE INVENTION

The object of this invention is to construct a winter sports eye mask capable of satisfying the aforesaid requirements and overcoming this problem.

Said object is achieved by an eye mask as described and claimed herein. Advantageous embodiments of the present invention are also described.

BRIEF DESCRIPTION OF THE FIGURES

The features and advantages of the mask according to this invention will become apparent from the following description, given by way of non-limiting example in accordance with the figures in the accompanying drawings, wherein.

DETAILED DESCRIPTION

Figure 1:
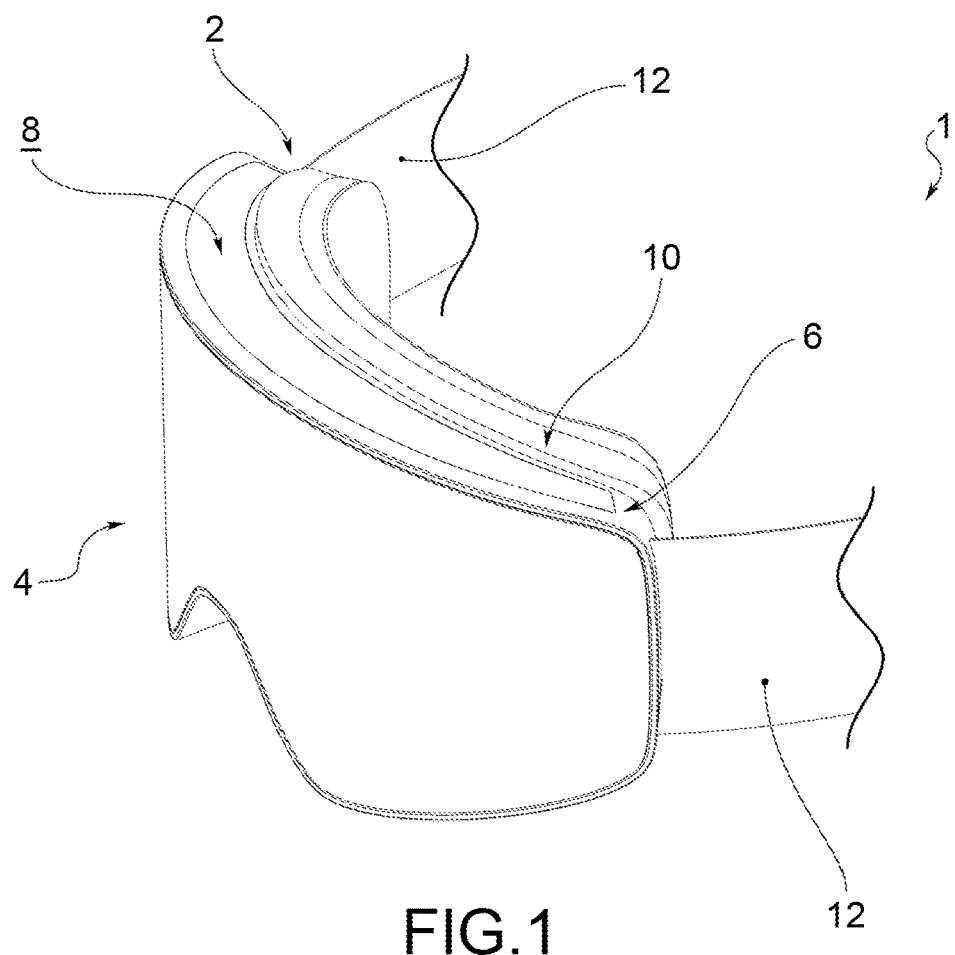
FIG. 1 shows a mask according to an embodiment of this invention.
Figure 2:
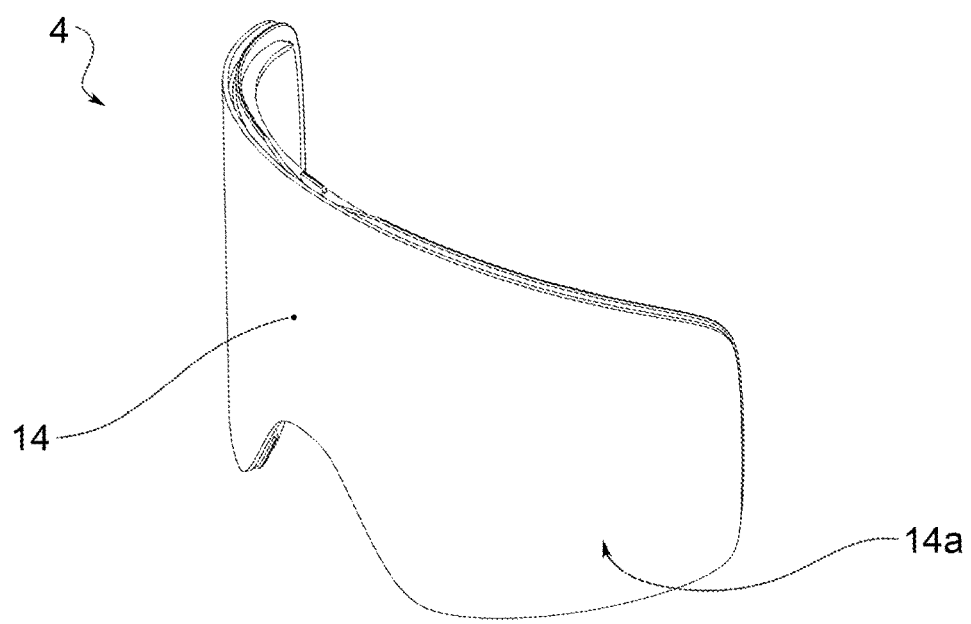
FIG. 2 shows a lens assembly of the mask in FIG. 1.
Figure 3:
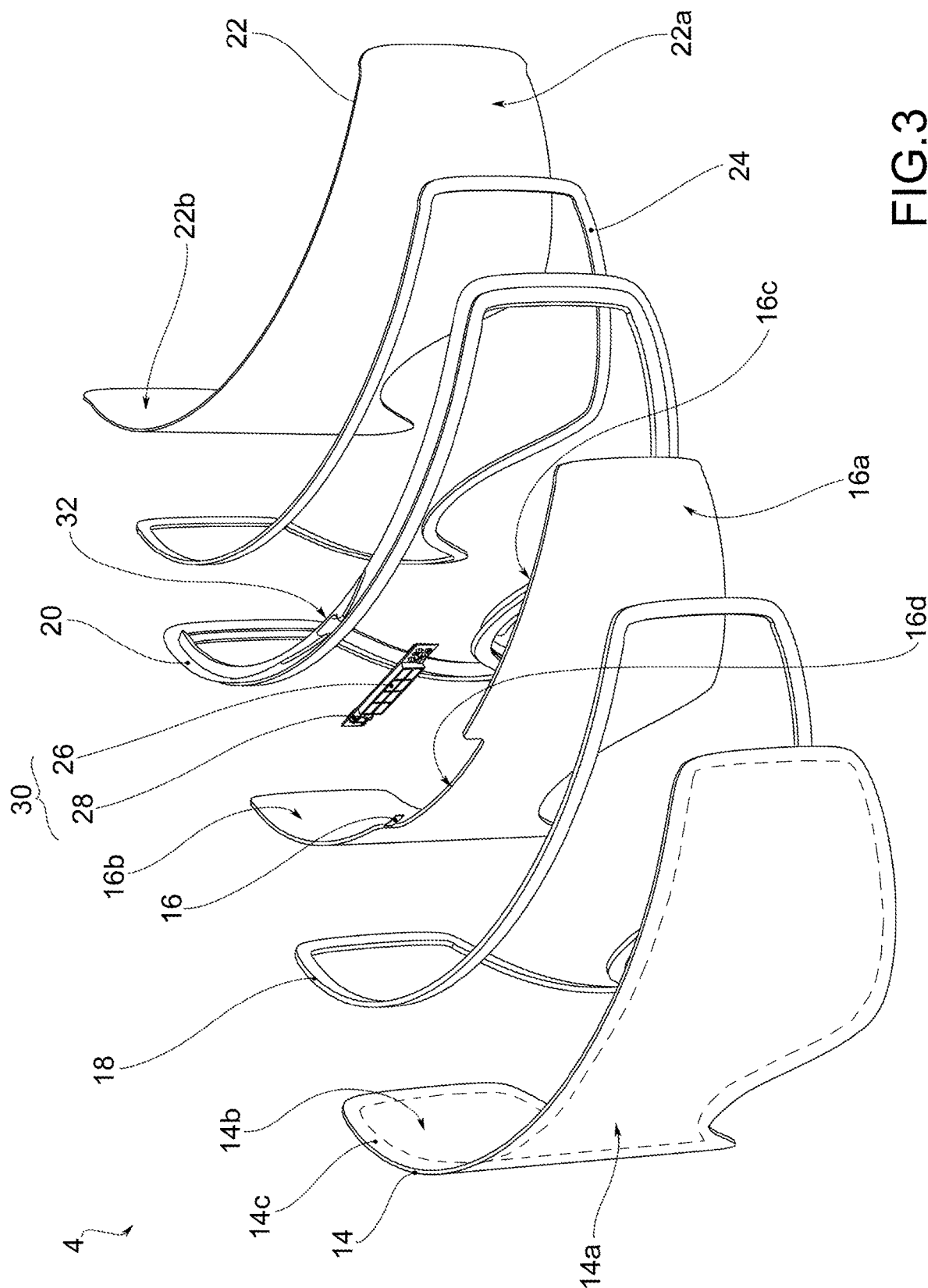
FIG. 3 illustrates the lens assembly of FIG. 2, in separate parts.
Figure 4:
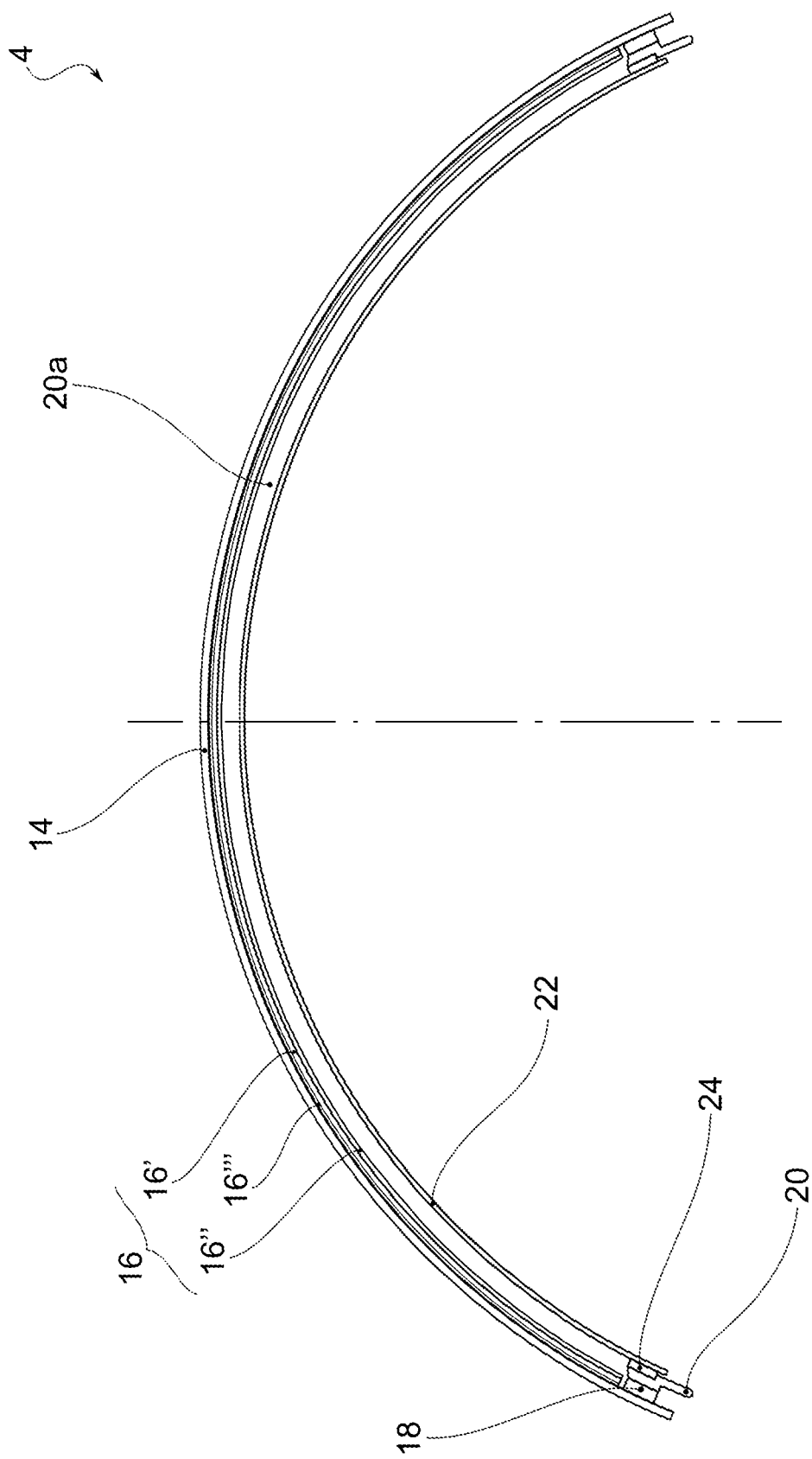
FIG. 4 depicts a plan view of the lens assembly from FIG. 2.
Figure 5:
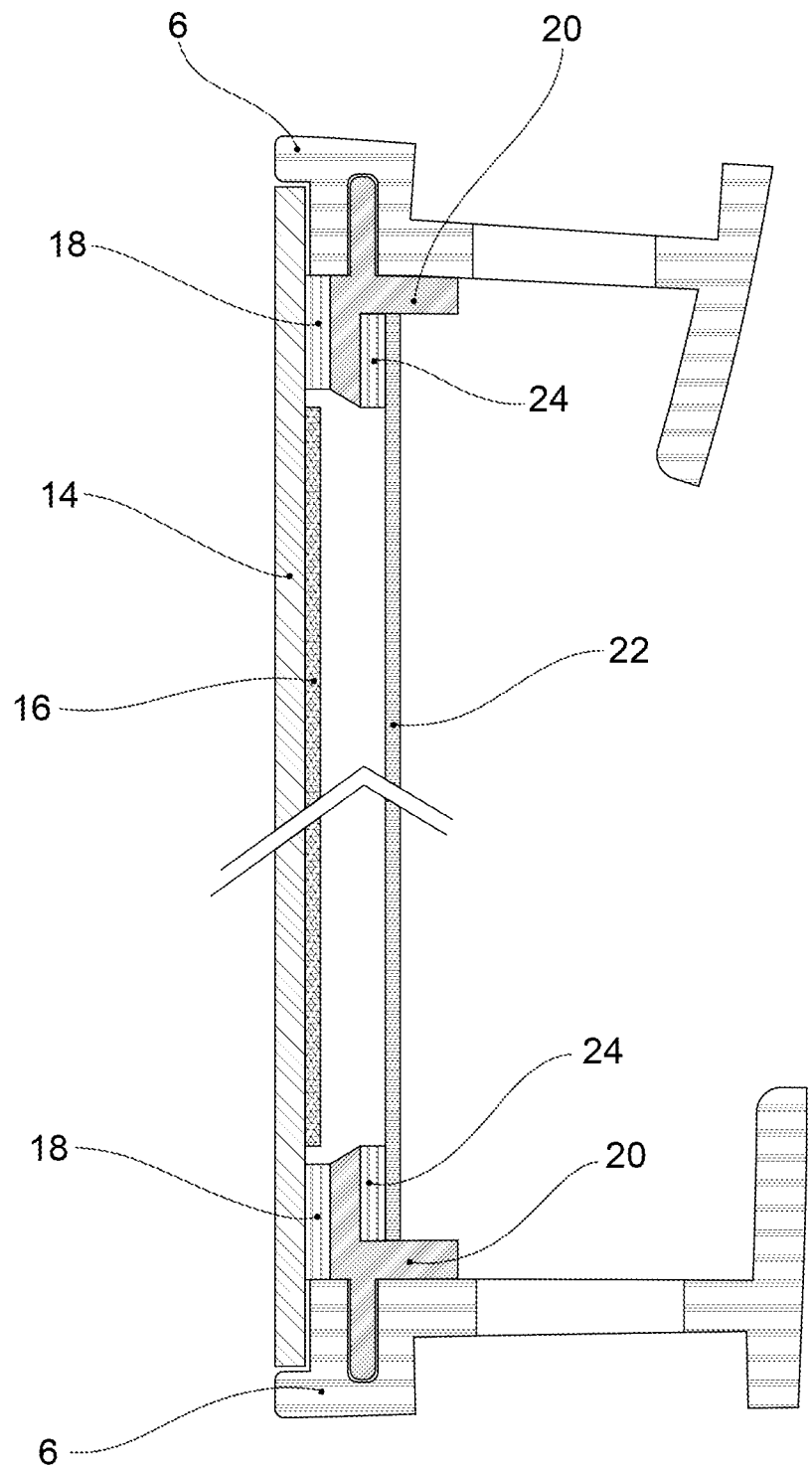
FIG. 5 is a schematic cross-sectional view of the mask.
Figure 6:
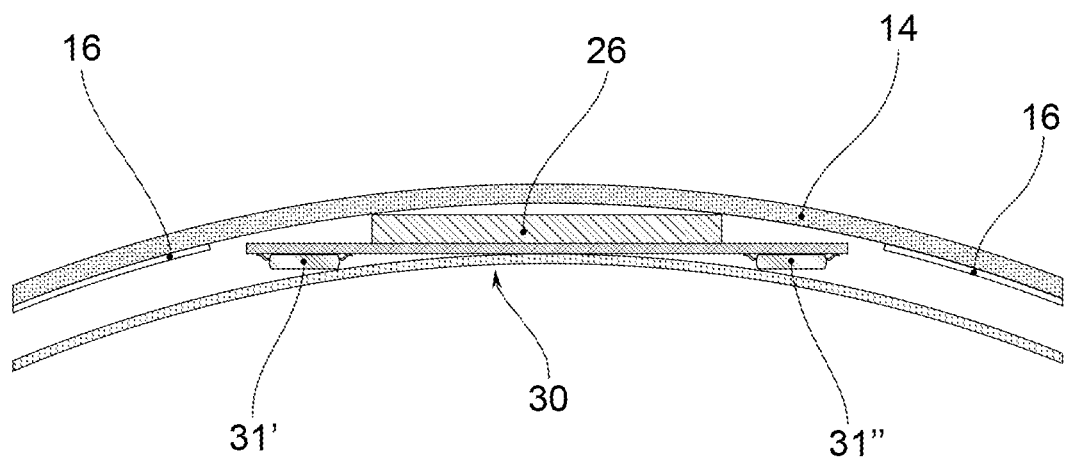
FIG. 6 is a cross-sectional view of a region of the mask, showing the placement of an electronic board.
Figure 7:
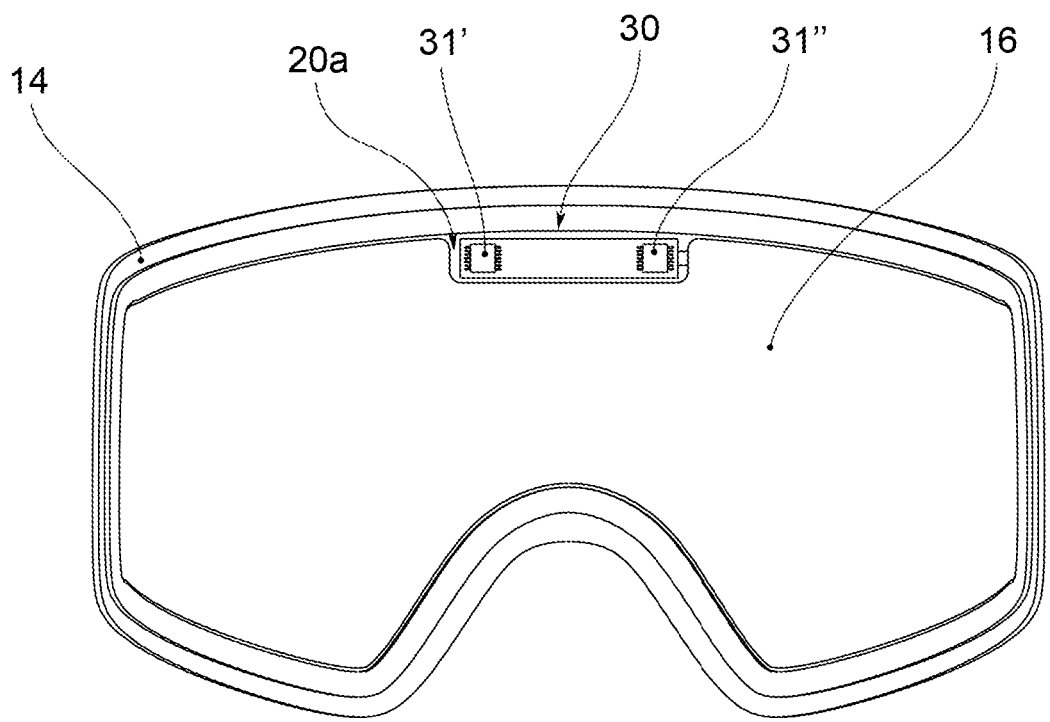
FIG. 7 shows the rear of the lens assembly with the electronic board.

With reference to the figures in the appended drawings, an eye protection mask for practicing winter sports, in particular alpine skiing according to an embodiment of this invention is collectively indicated by 1.

The mask 1 comprises a support assembly 2 and a lens assembly 4, attached to the support assembly 2.

The support assembly 2 comprises a support 6, generally made in one piece of a polymeric material, which is suitable for attaching the lens assembly 4, for example by means of an interlocking system.

Preferably, moreover, the support 6 has ventilation windows 8 for the entry of air into the mask; usually said ventilation windows are made at the top and/or bottom.

The support assembly 2 further comprises contact portions 10, usually made of foam or other soft material, placed peripherally to the support 6, internally with respect to the lens assembly 4, intended to contact and adhere to the face to limit the entry of air currents to the eyes.

Preferably, the mask 1 finally comprises an elastic band 12, typically attached to the sides of the support 6, for holding the mask on the face.

The lens assembly 4 comprises, according to a preferred embodiment, a structural lens 14 or outer lens, for example made of a plastic material, such as polycarbonate or polyamide; the structural lens 14 has an outer surface 14a and an inner surface 14b.

Preferably, the outer lens 14 has a transparency to electromagnetic radiation of wavelengths between 430 nm and 770 nm of between 54% and 70%. In particular, said transparency is preferably greater than 65% if only radiation between 565 nm and 770 nm is considered.

In addition, for example, the structural lens has a thickness between 0.8 millimeters and 1.6 millimeters, usually 1.2 millimeters.

The lens assembly 4 further comprises a liquid crystal film 16 (hereinafter LC film), provided with an outer face 16a, facing the structural lens 14, and
an inner face 16b.

The LC film 16 is applied to the structural lens 14, and in particular to the inner surface 14b thereof, preferably by lamination.

It should be noted that the term "lamination" means a process by which a first surface is joined to a second surface, facing the first, through the application of an adhesive layer distributed substantially over the entire extension of the two surfaces.

According to a preferred embodiment, the LC film template 16 is contained within the template of the structural lens 14, such that an adhesion zone 14c is peripherally defined on the inner surface 14b of the structural lens 14.

Preferably, the structural lens 14 has cylindrical curvature; advantageously, this allows optimal lamination of the LC film thereon, as well as giving a wrap-around shape suitable for using the mask for sports.

According to an embodiment, the LC film 16 is provided with an anti-fog treatment on the inner surface 16b.

The lens assembly 4 further comprises a frame 20, usually made in one piece, to which the structural lens 14 is attached at the front, via an outer double-sided tape 18, applied to the adhesion zone 14c of the inner surface 14b and the peripheral edge of the frame 20.

Lastly, the lens assembly 4 preferably comprises an inner lens 22, made of a single piece of polymeric material, having an outer surface 22a and an inner surface 22b.

The inner lens 22 is affixed to the frame 20, on opposite sides of the structural lens 14, for example by means of an inner double-sided tape 24 applied between the outer surface 22a of the inner lens 22 and the frame 20.

According to one aspect of the invention, the frame 20 is configured to exhibit greater stiffness than the stiffness of the structural lens 14.

For example, the frame 20 is made of a first material and the structural lens 14 is made of a second material, wherein the first material has a higher elasticity modulus than the second material. In this case, the increased frame stiffness is due to the inherent elasticity of the material.

For example, said frame is made of aluminum or other light alloys, for example by die casting, or of composite material, for example by injection molding, for example a polymeric material charged with glass fibers or carbon fibers. Preferably, said first material has an elasticity modulus greater than 28 GPa.

Advantageously, the frame 20, which is stiffer than the structural lens 14 and supports the LC film 16, allows the curvature of the structural lens to remain substantially unchanged and consequently prevents deformation of the LC film 16 as well.

Regarding the material of the frame, the Applicant has noted that traditional plastic materials are not per se sufficiently rigid to ensure a stable shape of the structural lens, which may have a transverse extension between 15 cm and 20 cm, unless such high thicknesses are used that they are not suitable for sports use.

Documents U.S. Pat. Nos. 9,335,565 and 5,172,256 only apparently seem to disclose a rigid-framed eye mask; in fact, they refer to structurally and functionally very different solutions from this invention.

Furthermore, according to the invention, the frame 20 is attached to the support 6, so that the stresses acting on the support are not transmitted to the structural lens 14, but to the frame 20, which will largely absorb them.

Preferably, moreover, the outer double-sided adhesive tape 18,
for example, made of acrylic material, has a thickness of between 0.5 millimeters and 2 millimeters.

This thickness is optimal between a thickness that is too low, which would imply that the structural lens has to fit exactly to the frame (so a small deformation of the frame or an inaccuracy in its production would result in a deformation of the structural lens), and a thickness that is too high, which would allow the structural lens to deform, making it too independent from the frame.

Advantageously, therefore, the deformability of the double-sided acrylic tape combined with the choice of thickness allow on the one hand to keep the curvature of the structural lens (and, consequently, of the LC film) unchanged, and on the other hand to create a sufficiently firm and rigid assembly with the frame, so as to prevent the structural lens from deforming.

It should be noted that the LC film is not in direct contact with the frame, which, however, indirectly increases the stiffness of the LC film through the interface with the double-sided tape, in embodiments that provide for it, and the structural lens.

Finally, the mask 1 comprises a photovoltaic cell 26 and an electronic circuit 28, powered by the photovoltaic cell 26, to command the LC film 16.

Preferably, the photovoltaic cell 26 and the electronic circuit 28 are arranged on the same support to form a single electronic board 30.

For example, a single photovoltaic cell is provided frontally, in a central area of the substrate, while two integrated circuits 31', 31" are positioned to the rear, laterally, on either side of the photovoltaic cell.

Advantageously, the photovoltaic cell is placed as close as possible to the structural lens, thus receiving more light; the electronic board, although rigid, actually takes a shape that follows that of the frame compartment; the use of a single electronic board allows for an easy replacement of the same in case of failure.

The photovoltaic cell 26 operates simultaneously as a sensor of the amount of light in the environment and as a power supply for the LC film; in effect, the greater the amount of light that strikes the photovoltaic cell, the higher the power generated by the photovoltaic cell; the power with which the LC film is fed is consequently higher and said LC lens darkens more.

Preferably, the electronic board 30 is supported by the frame 20, for example applied to a median portion 32 of the frame 20.

In particular, the electronic board 30 with the photovoltaic cell 26 is located between the structural lens 14 and the inner lens 22, in a sealed or leak-tight frame compartment 20a formed by the frame 20, the structural lens 14, and the inner lens 22; the photovoltaic cell 26 faces the structural lens 14.

The electronic board 30 with the photovoltaic cell 26 converts the direct current produced by the photovoltaic cell 26, for example, to square wave alternating current, and preferably limits the voltage applied to the LC film 16 to a predefined maximum threshold.

The frame compartment 20a forms a thermal gap that prevents fogging and protects the electronic board 30. To this end, preferably, the inner lens 22 undergoes an anti-fog treatment, characterized by an EN 166 7.3.2 test resistance of at least 8 seconds.

The LC film 16 has along an upper segment 16c of the peripheral edge a recess 16d at which the photovoltaic cell 26 is placed, so as to be struck by the light rays that pass only through the structural lens 14; the darkening of the LC film 16 does not therefore affect the operation of the photovoltaic cell 26,
although this photovoltaic cell 26
is placed under cover, in the frame compartment 20a.

In addition, the photovoltaic cell 26 benefits from any chromatic and mirroring filters placed on the structural lens 14, thus supplying the LC film according to what the user's eye perceives; for example, if the structural lens is provided with a mirroring filter that eliminates ultraviolet radiation, the photovoltaic cell will also not receive ultraviolet radiation, and consequently the LC film will not undergo variations in transparency according to ultraviolet radiation, as indeed it must.

The LC film 16, preferably, consists of a layer 16' with liquid crystals and dichroic pigments (LC layer 16', hereinafter) and two support layers 16", 16'", between which the LC layer 16' is placed, which contains the liquid crystals (which guide the orientation of the dichroic pigments), according to a production technology known as Guest-Host (GH technology), the advantages of which are illustrated in Italian patent application No. 10 2020 000 000 526, the teaching of which is explicitly incorporated herein.

However, the Applicant has noted that GH-type LC film is very sensitive to mechanical stresses, which may cause, for example, localized compression. The mask of the invention, in fact, being worn on the face, undergoes, once worn, an inevitable deformation to adapt to the shape and size of the user's face. Therefore, the use of a rigid frame according to this invention prevents the LC film from deforming, ensuring optimal vision.

According to an embodiment of the invention, the structural lens 14 is made by injection molding. Preferably, in said embodiment, the lens assembly 4 provides for a depolarizing material layer placed externally on the LC film 16, i.e., between the LC film 16 and the structural lens 14.

The depolarizing layer, e.g., a Panasonic MUAC4 film, advantageously allows for the nullification of optical interference effects between the structural lens 14, which routinely exhibits internal stresses due to injection molding, and the LC film 16, although GH-type LC film is less sensitive to such interference than TN-type LC films.

Advantageously, injection molding allows for a structural lens with variable thickness between center and sides ("corrected" lens), to improve optical definition (a possibility not offered by other lens manufacturing technologies, such as thermoforming), and the depolarizing layer cancels interference with internal stresses, providing optimal vision.

As is well known, certain lens absorption spectra allow for increased contrast perception in certain critical situations where perception of the shape of the snowy terrain becomes extremely difficult. The absorption spectra known to be most effective are perceived as orange or pink colors.

Obtaining these colorations by pigments would greatly reduce the transparency of the lens; this fact, in the context of this invention, could lead to having a lens assembly that is overall too dark since the total transparency depends on the product of the transparencies of all components of the lens assembly, including the LC film 16.

In order to achieve the desired transmission spectrum, at least two layers of deposits conferring a mirroring effect are present on the outer surface 14a of the structural lens 14, wherein said deposits exhibit a reflection spectrum having a maximum peak between 500 nm and 565 nm or between 430 nm and 480 nm so as to especially reflect blue/green light and thereby transmit more yellow/red light to favorably influence the transmission spectrum of the lens assembly.

More generally, according to a further embodiment, the mask comprises a polarizing film placed on the outside of a depolarizing film, for example in order to attenuate the reflection of the sun on the ground.

According to a variant embodiment, the frame has a greater stiffness than the structural lens by virtue of a particular structure, for example provided with ribs. For example, in such a variant, the frame comprises at least one rib at the top or bottom, such as to increase stiffness, such as bending stiffness.

It is clear that a person skilled in the art, in order to satisfy current needs, could make modifications to the mask described above, said modifications all being contained within the scope of protection as defined in the following claims.

What is claimed is:

1. An eye mask for practicing winter sports, the eye mask comprising a lens assembly and a support assembly, wherein the lens assembly comprises a frame, a structural lens, an inner lens having anti-fog properties, a Guest-Host-type liquid crystal (LC) film adapted to modify a transparency level thereof and laminated to the structural lens, and at least one electric source for supplying the LC film, wherein the structural lens is applied to the frame and the frame has a higher stiffness than the structural lens, wherein the support assembly comprises a support suitable for attaching the lens assembly, and wherein the inner lens is applied to the frame on a side opposite to the structural lens by a double-sided adhesive tape,
the eye mask further comprising a sealed frame compartment delimited by the structural lens, the frame, and the inner lens, wherein at least one electric source is placed in said sealed frame compartment.

2. The eye mask of claim 1, further comprising an outer double-sided adhesive tape adapted to couple peripherally the frame and the structural lens, wherein the frame is not in direct contact with the LC film.

3. The eye mask of claim 1, wherein the frame is made of a first material, the structural lens is made of a second material, and wherein the first material has a higher elasticity modulus than the second material.

4. The eye mask of claim 3, wherein the frame is made of aluminum or other light alloys or of composite or reinforced plastic material.

5. The eye mask of claim 1, wherein the structural lens is made of polycarbonate or polyamide.

6. The eye mask of claim 1, wherein the support has a lower stiffness than the frame.

7. The eye mask of claim 1, wherein the structural lens is made by injection molding.

8. The eye mask of claim 1, further comprising a depolarizing film placed between the LC film and the structural lens.

9. The eye mask of claim 1, wherein said at least one electric source is a photovoltaic cell.

10. The eye mask of claim 9, further comprising an electronic board placed inside the structural lens comprising:
a board support having a front face and a rear face;
said photovoltaic cell assembled in a central zone of the front face of the board support; and
at least one integrated circuit assembled in a side zone of the rear face of the board support.

11. The eye mask of claim 1, wherein said structural lens has a transparency between 54% and 70% to electromagnetic radiation with a wavelength between 430 nm and 770 nm.

12. The eye mask of claim 1, wherein said structural lens has a transparency higher than 65% to electromagnetic radiation with a wavelength between 565 nm and 770 nm.

13. The eye mask of claim 1, wherein at least two layers of deposits, giving a mirroring effect, are present on an outer surface of the structural lens, and wherein said deposits have a reflection spectrum with a maximum peak between 500 nm and 565 nm or between 430 nm and 480 nm.

14. The eye mask of claim 1, wherein the eye mask comprises a polarizing film placed outside a depolarizing film or wherein the structural lens is polarizing or wherein the structural lens is made by laminating a polarizing film.

15. The eye mask of claim 1, wherein the support is made of a single piece of polymeric material.

16. The eye mask of claim 1, wherein the support is suitable for attaching the lens assembly by an interlocking system.

17. The eye mask of claim 1, wherein the support has one or more ventilation windows defined through at least one of the top of the support or the bottom of the support, for the entry of air into the eye mask.

18. The eye mask of claim 1, wherein the support assembly further comprises contact portions configured to contact a face of a wearer of the eye mask, to limit the entry of air currents to eyes of the wearer.

* * * * *